US011517328B2

United States Patent
Adams et al.

(10) Patent No.: US 11,517,328 B2
(45) Date of Patent: Dec. 6, 2022

(54) FORCE ABSORPTION SYSTEM FOR DISPOSABLE SHAVERS AND BURRS

(71) Applicant: Arthrex, Inc., Naples, FL (US)

(72) Inventors: Ken Adams, Naples, FL (US); Michael Barican, Naples, FL (US); Phil O'Quinn, Naples, FL (US); Benjamin P. Hedges, Santa Barbara, CA (US); Martin A. Frith, Golela, CA (US)

(73) Assignee: ARTHREX, INC., Naples, FL (US)

( * ) Notice: Subject to any disclaimer, the term of this patent is extended or adjusted under 35 U.S.C. 154(b) by 580 days.

(21) Appl. No.: 16/358,055

(22) Filed: Mar. 19, 2019

(65) Prior Publication Data

US 2020/0297354 A1 Sep. 24, 2020

(51) Int. Cl.
  *A61B 17/16* (2006.01)
  *A61B 17/00* (2006.01)
  *A61B 17/32* (2006.01)
  *A61M 1/00* (2006.01)

(52) U.S. Cl.
  CPC .... *A61B 17/1631* (2013.01); *A61B 17/00234* (2013.01); *A61B 17/1622* (2013.01); *A61B 17/32002* (2013.01); *A61M 1/76* (2021.05); *A61B 2017/0046* (2013.01)

(58) Field of Classification Search
  CPC ............ A61B 17/1615; A61B 17/1617; A61B 17/1622; A61B 17/1624; A61B 17/1626; A61B 17/1628; A61B 17/1631; A61B 17/1633; A61B 17/32002
  See application file for complete search history.

(56) References Cited

U.S. PATENT DOCUMENTS

| 4,428,443 | A | * | 1/1984 | Oliphant ................ E21B 17/07 |
| | | | | 175/321 |
| 5,499,984 | A | | 3/1996 | Steiner et al. |
| 5,709,698 | A | | 1/1998 | Adams et al. |
| 5,713,905 | A | | 2/1998 | Goble et al. |
| 5,833,692 | A | | 11/1998 | Cesarini et al. |
| 6,045,564 | A | | 4/2000 | Walen |

(Continued)

FOREIGN PATENT DOCUMENTS

| CH | 710378 | 5/2016 |
| EP | 1361830 | 5/2004 |

(Continued)

OTHER PUBLICATIONS

North Grove Enterprise, "Web A," northgroveenterprise.com, Weber, accessed: Jul. 2018.

(Continued)

*Primary Examiner* — Si Ming Ku
(74) *Attorney, Agent, or Firm* — Greenberg Traurig LLP; Michael K. Dixon (57) ABSTRACT

A drive system for a handheld rotary medical device including a force absorption system incorporated in a drive coupling of the drive system is disclosed. The force absorption system may be included in the drive coupling whereby force absorption system absorbs linear forces aligned with a longitudinal axis of the drive coupling. As such, the force absorption system permits limited linear movement of a rotary surgical implement, which may be a shaver, burr or the like, relative to a drive shaft and handheld housing.

19 Claims, 8 Drawing Sheets

(56) References Cited

U.S. PATENT DOCUMENTS

| | | |
|---|---|---|
| 6,176,703 B1 | 1/2001 | Gugel et al. |
| 6,328,752 B1 | 12/2001 | Sjostrom et al. |
| 6,494,892 B1 | 12/2002 | Ireland et al. |
| 6,517,560 B1 | 2/2003 | Toth et al. |
| 6,783,533 B2 | 8/2004 | Green et al. |
| 6,863,478 B2 | 3/2005 | Steiger et al. |
| 7,060,071 B2 | 6/2006 | Steiger |
| 7,214,060 B2 | 5/2007 | Ma |
| 7,226,459 B2 | 6/2007 | Cesarini et al. |
| 7,513,899 B2 | 4/2009 | Grim |
| 7,922,737 B1 | 4/2011 | Cesarini et al. |
| 7,993,360 B2 | 8/2011 | Hacker et al. |
| 8,137,362 B2 | 3/2012 | Malinowski |
| 8,177,803 B2 | 5/2012 | Heisler |
| 8,313,502 B2 | 11/2012 | Heisler |
| 8,491,586 B2 | 7/2013 | Lechot et al. |
| 8,756,819 B2 | 6/2014 | Whited et al. |
| 8,931,388 B2 | 1/2015 | Jezierski |
| 8,961,519 B2 | 2/2015 | Gillard et al. |
| 9,232,958 B2 | 1/2016 | Jezierski et al. |
| 9,402,638 B2 | 8/2016 | Del et al. |
| 9,468,455 B2 | 10/2016 | Jezierski et al. |
| 9,480,484 B2 | 11/2016 | Loreth et al. |
| 9,668,762 B2 | 6/2017 | Shener-Lrmakoglu et al. |
| 9,763,680 B2 | 9/2017 | Fritzinger et al. |
| 9,844,408 B2 | 12/2017 | Edwards et al. |
| 9,924,955 B2 | 3/2018 | Weekes et al. |
| 9,949,737 B2 | 4/2018 | Zergiebel et al. |
| 2005/0065538 A1 | 3/2005 | Van |
| 2006/0142776 A1 | 6/2006 | Iwanari |
| 2007/0299459 A1 | 12/2007 | Way et al. |
| 2008/0071303 A1 | 3/2008 | Hacker et al. |
| 2009/0048485 A1 | 2/2009 | Heisler |
| 2010/0036403 A1 | 2/2010 | O'Quinn et al. |
| 2010/0249786 A1 | 9/2010 | Schmiedling et al. |
| 2011/0071527 A1* | 3/2011 | Nelson .............. A61B 17/1624 606/85 |
| 2011/0202023 A1 | 8/2011 | Stanton et al. |
| 2013/0304070 A1 | 11/2013 | Nelson et al. |
| 2014/0140815 A1 | 5/2014 | Shener-Irmakoglu et al. |
| 2016/0278802 A1 | 9/2016 | Cihak et al. |
| 2016/0302930 A1 | 10/2016 | Axelrod et al. |
| 2017/0095260 A1 | 4/2017 | Masson |
| 2017/0265874 A1 | 9/2017 | Hwang |
| 2018/0028212 A1 | 2/2018 | Akilian et al. |
| 2018/0036026 A1 | 2/2018 | Inamdar |
| 2018/0242962 A1 | 8/2018 | Walen et al. |
| 2018/0325527 A1 | 11/2018 | Wozencroft |

FOREIGN PATENT DOCUMENTS

| | | |
|---|---|---|
| WO | 0122890 | 4/2001 |
| WO | 2016186943 | 11/2016 |

OTHER PUBLICATIONS

Kavo Dental Excellence, "EXPERTmatic E25," kavo.com, accessed: Jul. 2018.

United States Patent and Trademark Office; PCT International Search Report, issued in connection to application No. PCT/US20/23338; dated Aug. 18, 2020; 5 pages; US.

United States Patent and Trademark Office; PCT Written Opinion of the International Searching Authority, issued in connection to application No. PCT/US20/23338; dated Aug. 18, 2020; 11 pages; US.

* cited by examiner

FORCE ABSORPTION SYSTEM FOR DISPOSABLE SHAVERS AND BURRS

FIELD OF THE INVENTION

The disclosure relates generally to handheld, rotary medical devices, and more particularly, to handheld, rotary medical devices with disposable shavers and burrs.

BACKGROUND

Handheld rotary medical devices typically include detachable working ends, which are often shavers or burrs. The detachable working ends are typically attached to the handheld devices via any one of numerous releasable connection systems. The releasable connection systems enable the detachable working ends to be quickly and easily removed and replaced or exchanged. The releasable connection systems also enable disposable working ends to be effective and to be easily replaced.

SUMMARY OF THE INVENTION

A drive system for a handheld rotary medical device including a force absorption system incorporated in a drive coupling of the drive system is disclosed. The force absorption system may be included in the drive coupling whereby force absorption system absorbs linear forces aligned with a longitudinal axis of the drive coupling. As such, the force absorption system permits limited linear movement of a rotary surgical implement, which may be a shaver, burr or the like, relative to a drive shaft and handheld housing.

In at least one embodiment, a drive system for a handheld rotary medical device includes a drive coupling configured to be positioned between a drive motor and a rotary surgical implement and a force absorption system incorporated in the drive coupling whereby force absorption system absorbs linear forces aligned with a longitudinal axis of the drive coupling. The force absorption system may be formed from a hollow, cylindrical, proximal end of the drive coupling, wherein material forming the hollow, cylindrical, proximal end of the drive coupling includes a plurality of relief slots and an engagement protrusion positioned in the hollow, cylindrical, proximal end for engaging a drive shaft of the drive system. Adjacent relief slots of the plurality of relief slots may be offset circumferentially from each other. The plurality of relief slots may be organized into rows, whereby at least one row includes at least two relief slots that each span about one quarter of a circumference of the drive coupling. The rows of relief slots may each include at least two relief slots that each span one quarter of a circumference of the drive coupling, wherein relief slots are offset circumferentially from adjacent rows of relief slots.

In at least one embodiment, the force absorption system may be formed from a hollow, cylindrical, proximal end of the drive coupling and may include a plurality of force transmitting tabs extending proximally from the proximal end of the drive coupling. The force transmitting tabs may include angled proximal ends configured to engage an angled drive surface such that a linear force applied to the force absorption system toward the angled drive surface causes the force transmitting tabs to deflect radially outward. The force absorption system may include an engagement protrusion positioned in the hollow, cylindrical, proximal end for engaging a drive shaft of the drive system. The force transmitting tabs may be positioned 180 degrees apart.

In at least one embodiment, the force absorption system may be formed from a cylindrical proximal end of the drive coupling that includes an engagement protrusion extending proximally from the proximal end for engaging a drive shaft of the drive system and at least one force absorber on the proximal end of the drive coupling on each side of the engagement protrusion configured to contact a drive shaft. The force absorber may be, but is not limited to being, a leaf spring.

In at least one embodiment, the force absorption system may be formed from a hollow, cylindrical, proximal end of the drive coupling, wherein material forming the hollow, cylindrical, proximal end of the drive coupling includes a plurality of relief slots forming wings and an engagement protrusion positioned in the hollow, cylindrical, proximal end for engaging a drive shaft of the drive system.

In at least one embodiment, the force absorption system may be formed from a hollow, cylindrical, proximal end of the drive coupling and may include a plurality of pegs extending proximally from a proximal end of the drive coupling and configured to contact a drive shaft of the drive system. At least one of the pegs may be formed from a base portion that is aligned with the proximal end of the drive coupling and a tip portion that is angled radially inward from the base portion. The plurality of pegs may include four pegs, each formed from the base portion that is aligned with the proximal end of the drive coupling and the tip portion that is angled radially inward from the base portion. Each of the pegs may be positioned 90 degrees circumferentially from an adjacent peg on the proximal end of the drive coupling.

In at least one embodiment, the force absorption system may be formed from a hollow, cylindrical, proximal end of the drive coupling. A shock absorber may be positioned within a hollow chamber of the proximal end and exposed to contact a drive shaft of the drive system. The force absorption system may include a plurality of tabs extending radially inward from an inner surface of the hollow chamber to engage receivers in the drive shaft of the drive system. In at least one embodiment, the shock absorber may be a coil spring.

In at least one embodiment, the force absorption system may be formed from a cylindrical, proximal end of the drive coupling, a flange extending radially outward from an outer surface of the cylindrical, proximal end of the drive coupling and a shock absorber coupled to the proximal end of the drive coupling. In at least one embodiment, the shock absorber may be a coil spring. The coil spring may at least partially encompasses the drive coupling at the proximal end.

An advantage of the force absorption system is that the force absorption system aligns the disposable instrument with the motor drive.

Another advantage of the force absorption system is that the force absorption system provides axial force to the inner member of the disposable to maintain the position of the distal cutting member.

Yet another advantage of the force absorption system is that the force absorption system reduces tolerance stack-ups between the disposable and the motor drive.

Another advantage of the force absorption system is that the force absorption system provides a method to minimize the effects of runout between the inner hub and motor drive.

Still another advantage of the force absorption system is that the force absorption system is a low cost method of providing the benefits listed above while minimizing the number of components, such as by eliminating the need for a spring retainer.

These and other embodiments are described in more detail below.

DETAILED DESCRIPTION OF THE FIGURES

As shown in FIGS. 1-24, a drive system 10 for a handheld rotary medical device 12 including a force absorption system 14 incorporated in a drive coupling 16 of the drive system 10 is disclosed. The force absorption system 14 may be included in the drive coupling 16 whereby force absorption system 14 absorbs linear forces aligned with a longitudinal axis 18 of the drive coupling 16. As such, the force absorption system 14 permits limited linear movement of a rotary surgical implement 20, which may be a shaver, burr or the like, relative to a drive shaft 22 and handheld housing 24.

In at least one embodiment, the drive system 10 may be configured for a handheld rotary medical device 12. The drive system 10 may include a drive coupling 16 configured to be positioned between a drive motor 26 and a rotary surgical implement 20. The drive system 10 may also include a force absorption system 14 incorporated in the drive coupling 16 whereby the force absorption system 14 absorbs linear forces aligned with the longitudinal axis 18 of the drive coupling 16.

Figure 1:
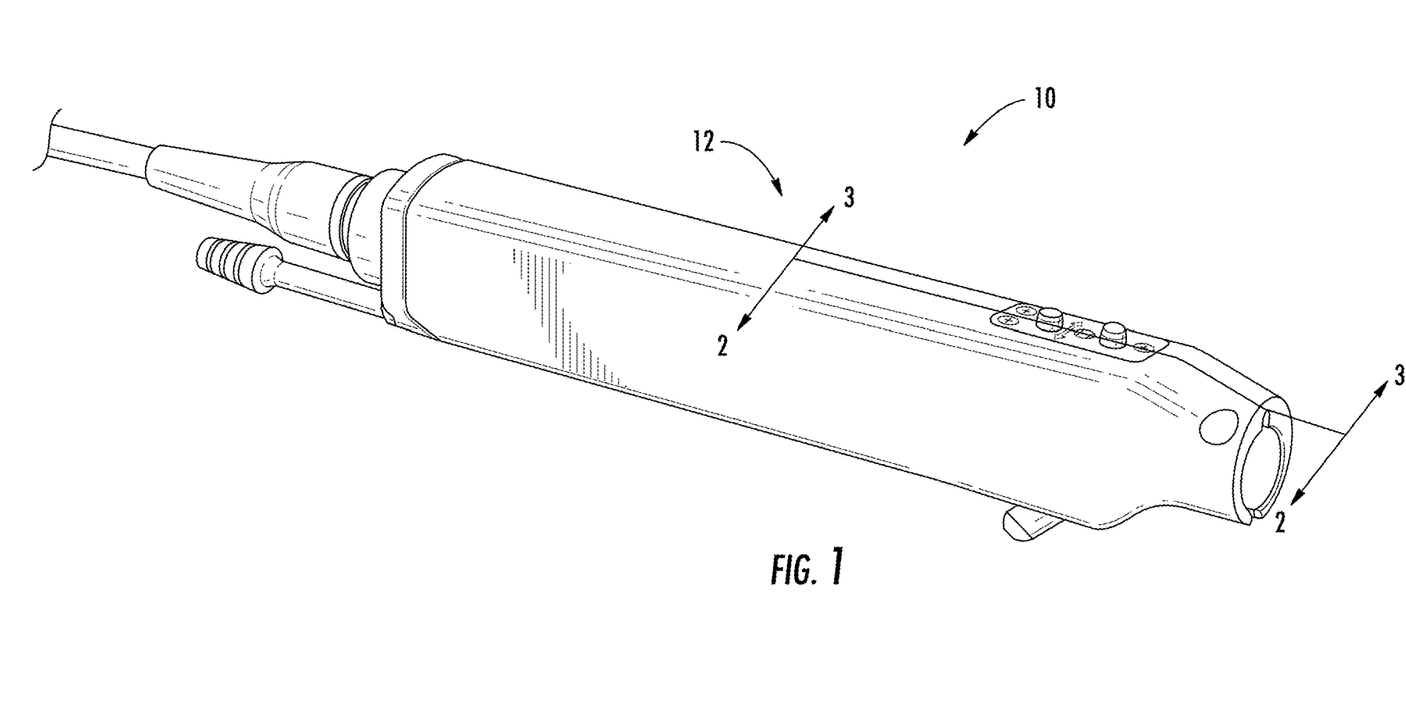
FIG. 1 is a perspective view of a handheld rotary medical device configured to receive a drive coupling of a drive system including a force absorption system.
Figure 2:
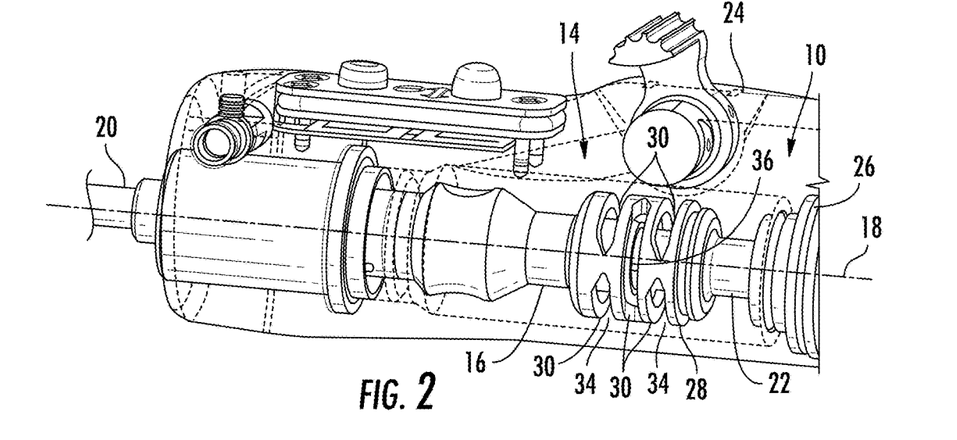
FIG. 2 is a cross-sectional view of a portion of the handheld rotary medical device of FIG. 1 taken alone section line 2-2.
Figure 3:
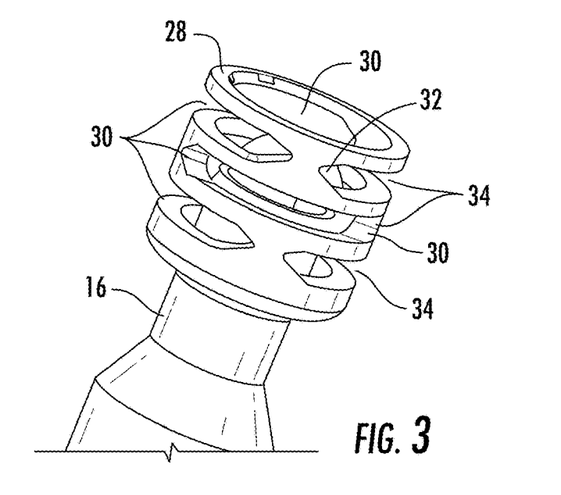
FIG. 3 is a partial perspective view of a proximal end of the drive coupling with force absorption system of FIG. 2.
Figure 4:
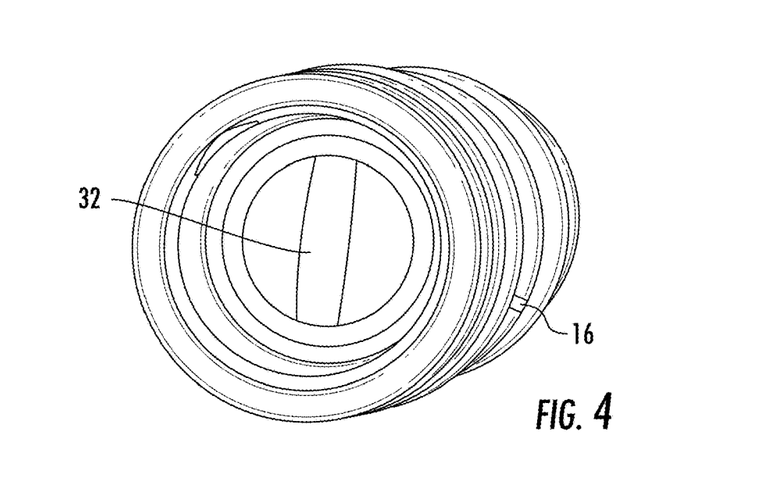
FIG. 4 is another perspective view of the proximal end of the drive coupling with force absorption system of FIG. 3.

In at least one embodiment, as shown in FIGS. 2-4, the force absorption system 14 may be formed from a hollow, cylindrical, proximal end 28 of the drive coupling 16. Material forming the hollow, cylindrical, proximal end 28 of the drive coupling 16 may include at least one relief slot 30 configured to deflect when placed under linear force enabling linear movement of the drive coupling 16 relative to a drive shaft 22 of the drive system 10. The relief slot 30 may be generally elongated in shape and may be rectangular, oval, elliptical and the like. The corners forming the relief slot 30 may be rounded. The relief slot may be positioned to extend generally circumferentially around the drive coupling 16, which in at least one embodiment may be generally orthogonal to the longitudinal axis 18 of the drive coupling 16. The circumferential length of the relief slot 30 may be any appropriate length. In at least one embodiment, the circumferential length of the relief slot 30 may be between about one eighth and three quarters of a circumferential length of the drive coupling 16 and in at least one embodiment, between one quarter and one half of a total circumference of the drive coupling 16.

In at least one embodiment, the force absorption system 14 may include a plurality of relief slots 30, as shown in FIGS. 2 and 3. The plurality of relief slots 30 may be configured such that adjacent relief slots 30 of the plurality of relief slots 30 are offset circumferentially from each other. The plurality of relief slots 30 may be organized into rows 34 of one or more relief slots 30. The rows 34 may be separated linearly, and the rows 34 may extend circumferentially around the drive coupling 16. In at least one embodiment, two or more relief slots 30 may be organized into a row 34. The plurality of relief slots 30 forming a single row 34 may extend end to end circumferentially around the drive coupling 16. The plurality of relief slots 30 forming a single row 34 may each be between about one eighth and one half of a circumferential length of the drive coupling 16, and in at least one embodiment, may be between one eighth and one half of a circumferential length of the drive coupling 16, such as, but not limited to being one quarter of a circumference of the drive coupling 16. The adjacent relief slots 30 in adjacent rows 34 may be offset circumferentially from relief slots 30 in adjacent rows 34. In at least one embodiment, adjacent rows 34 of relief slots 30 may be offset circumferentially between about 20 degrees and about 180 degrees, and in at least one embodiment, may be offset circumferentially about 90 degrees. The relief slots 30 in adjacent rows 34 on either side of a single row 34 may be aligned with each other, and the relief slots 34 forming the middle row 34 may be offset relative to the two adjacent rows 34. There may be any appropriate number of rows 34 of relief slots 30 in the drive coupling 16. In at least one embodiment, the drive coupling 16 may include between one and six rows 34, and in particular, and not by way of limitation, may include three rows 34 of relief slots 30.

As shown in FIGS. 3 and 4, the force absorption system 14 may include an engagement protrusion 32 positioned in the hollow, cylindrical, proximal end 28 for engaging a drive shaft 22 of the drive system 10. The engagement protrusion 32 may have any appropriate configuration for transferring rotary motion from the drive shaft 22 to the drive coupling 16 via the engagement protrusion 32. In at least one embodiment, the drive shaft 22 may include a slot 36 for receiving the engagement protrusion 32. The engagement protrusion 32 may have rounded edges and may have a rounded end to facilitate smooth insertion into the slot 36 in the drive shaft 22.

Figure 24:
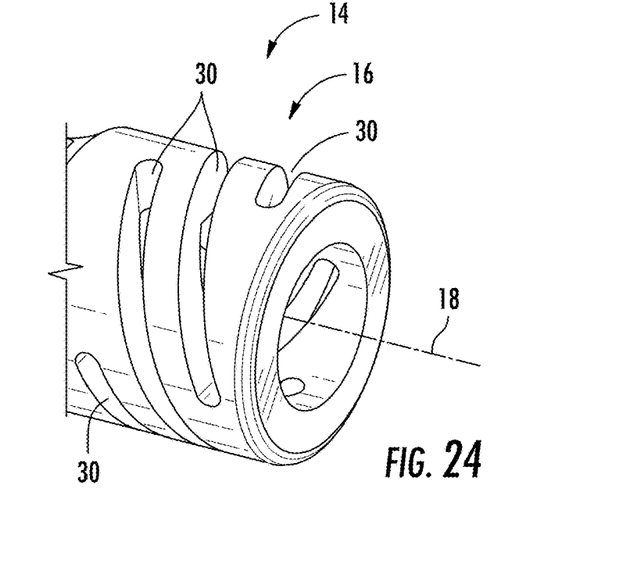
FIG. 24 is a perspective view of another configuration of a proximal end of the drive coupling with force absorption system of FIG. 2.

In another embodiment, as shown in FIG. 24, the force absorption system 14 may be formed similarly to the embodiment shown in FIGS. 2-4, except that the relief slots may have another configuration. As such, the embodiment shown in FIG. 24 may include the elements listed above and shown in shown in FIGS. 2-4 and are discussed in detail here. Rather, the description above is incorporated herein for a description of FIG. 24. In addition, one or more of the relief slots 30 of the force absorption system 14 of FIG. 24 may be positioned nonorthogonal and nonparallel to the longitudinal axis 18 of the drive coupling 16. The relief slots 30 may form a helical configuration such that the relief slots 30 are angled relative to the longitudinal axis 18 of the drive coupling 16 as the relief slots 30 extend circumferentially around the drive coupling 16. The relief slots 30 may be aligned parallel to each other. In other embodiments, one or more of the helical relief slots 30 may be misaligned relative to each other.

Figure 5:
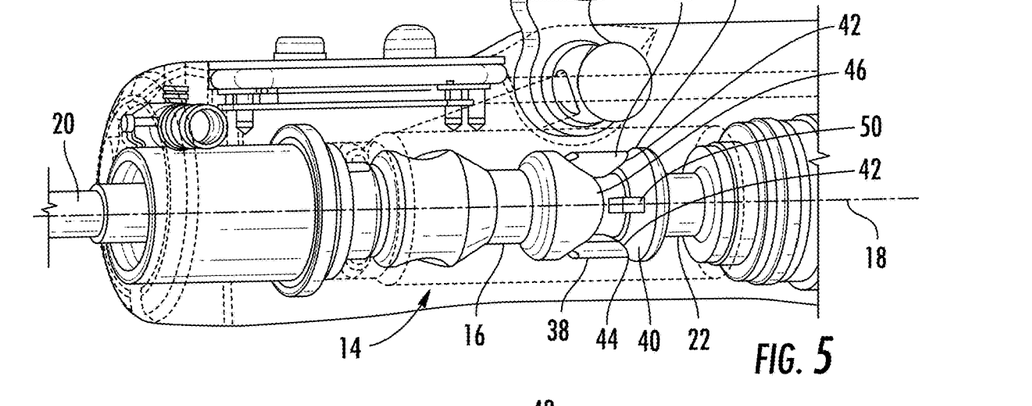
FIG. 5 is a cross-sectional view of a portion of the handheld rotary medical device of FIG. 1 with another embodiment of the force absorption system taken alone section line 2-2.
Figures 6, 7:
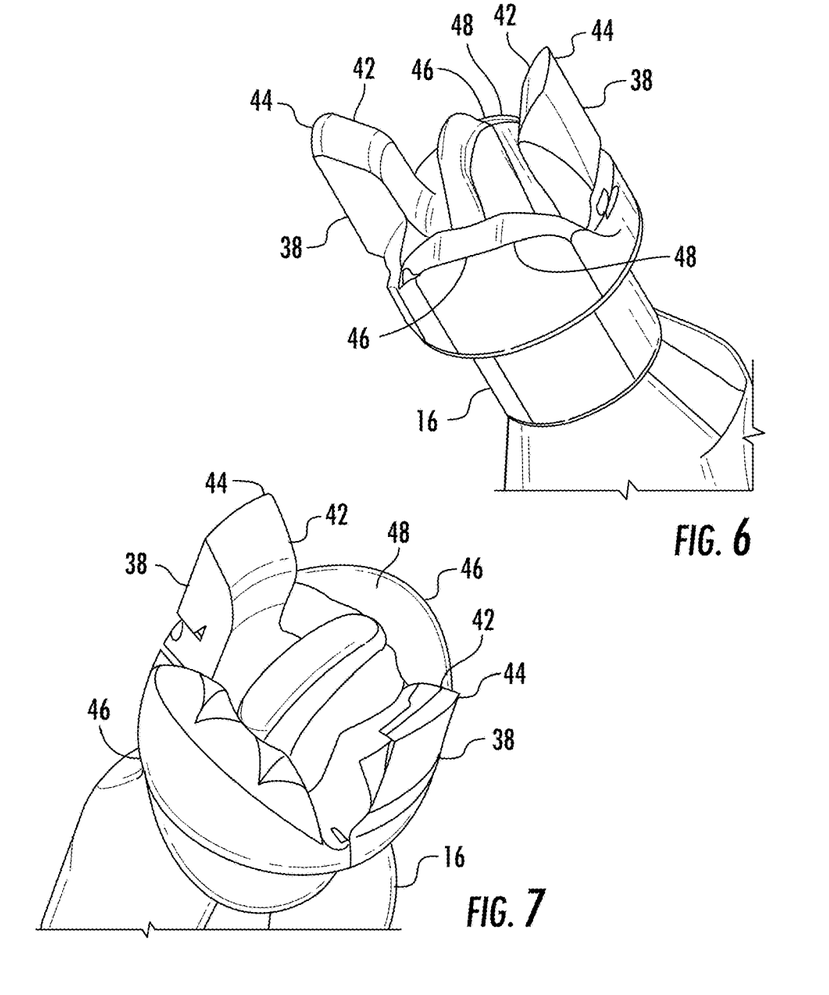
FIG. 6 is a partial perspective view of a proximal end of the drive coupling with force absorption system of FIG. 5.
FIG. 7 is another perspective view of the proximal end of the drive coupling with force absorption system of FIG. 6.

In another embodiment of the drive coupling 16, as shown in FIGS. 5-7, the force absorption system 14 may be formed from a hollow, cylindrical, proximal end 28 of the drive coupling 16 and may include a plurality of force transmitting tabs 38 extending proximally from the proximal end 28 of the drive coupling 16. The force transmitting tabs 38 may include angled proximal ends 28 configured to engage an angled drive surface 40 such that a linear force applied to the force absorption system 14 toward the angled drive surface 40 causes the force transmitting tabs 38 to deflect radially outward permitting limited linear movement of the drive coupling 16 along the longitudinal axis 18 of the drive coupling 16. Flexing of the force transmitting tabs 38 radially outwardly creates a force stored within the tabs 38 that when a force is removed from the drive coupling 16 forcing it in a proximal direction, the flexed tabs 38 move the drive coupling 16 linearly in a distal direction along the longitudinal axis 18 of the drive coupling 16.

The force transmitting tabs 38 may have any appropriate configuration. In at least one embodiment, the force transmitting tabs 38 may have angled contact surfaces 42 configured to contact the angled drive surface 40. The angled contact surface 42 of the force transmitting tab 38 may be configured such that the tab 38 includes a tip 44 on the tab 38 whereby the tip 44 is on a radially outermost portion of the tab 38. The angled contact surface 42 of the force transmitting tab 38 may extend radially inwardly from the tip 44. In at least one embodiment, the angled contact surface 42 of the force transmitting tab 38 may also extend distally from the tip 44. The corresponding the angled drive surface 40 may have an angled surface that has a distal diameter that is smaller than a proximal diameter. The angled drive surface 40 may be positioned within the drive system 10 such that the force transmitting tabs 38 contact the angled drive surface 40 when the drive coupling 16 is moved linearly along the longitudinal axis 18 of the drive coupling 16. The angled drive surface 40 may be a conical surface with a longitudinal axis aligned with the longitudinal axis 18 of the drive coupling 16.

The drive coupling 16 may include one or more force transmitting tabs 38. In at least one embodiment, the drive coupling 16 may include two or more force transmitting tabs 38. In one embodiment with two force transmitting tabs 38, the force transmitting tabs 38 may be positioned 180 degrees apart. In embodiments with more than two force transmitting tabs 38, the force transmitting tabs 38 may be spaced equidistant from each other or in alternative configurations.

The drive coupling 16 may include one or more stops 46 configured to limit the amount of linear movement of the drive coupling 16 along the longitudinal axis 18. In at least one embodiment, as shown in FIGS. 5 and 6, the drive coupling 16 may include two stops 46. The stops 46 may be separated from each other with each stop 46 being positioned between the force transmitting tabs 38. The stops 46 may be positioned adjacent radially outer surfaces of the drive coupling 16, similar to the force transmitting tabs 38. The stops 42 may be configured with curved surfaces 48 that contact protrusions 50 from the angled drive surface 40. In at least one embodiment, the protrusions 50 may be positioned about 180 degrees apart on the angled drive surface 40.

The drive coupling shown in FIGS. 6 and 7 may also include an engagement protrusion 32 positioned in the hollow, cylindrical, proximal end 28 for engaging a drive shaft 22 of the drive system 10. The engagement protrusion 32 shown in FIG. 2 may be similar to the engagement protrusion 32 shown in FIGS. 3 and 4.

Figure 8:
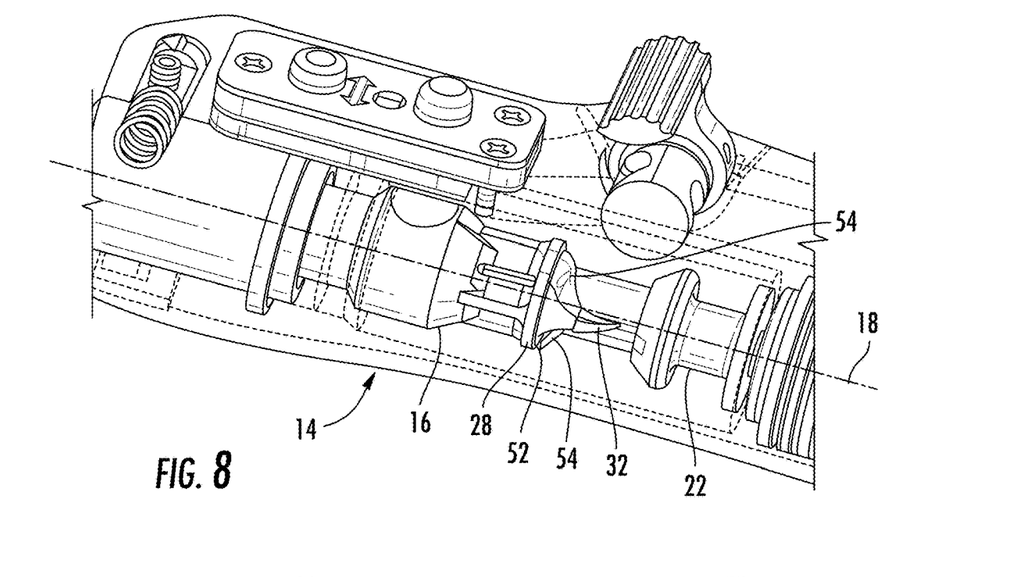
FIG. 8 is a cross-sectional view of a portion of the handheld rotary medical device of FIG. 1 with yet another embodiment of the force absorption system taken alone section line 2-2.
Figure 9:
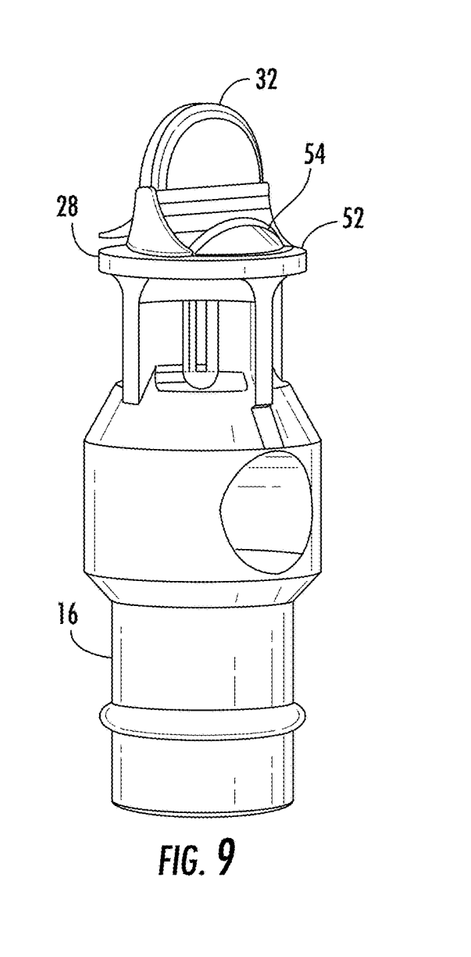
FIG. 9 is a partial perspective view of the drive coupling with force absorption system of FIG. 8.
Figure 10:
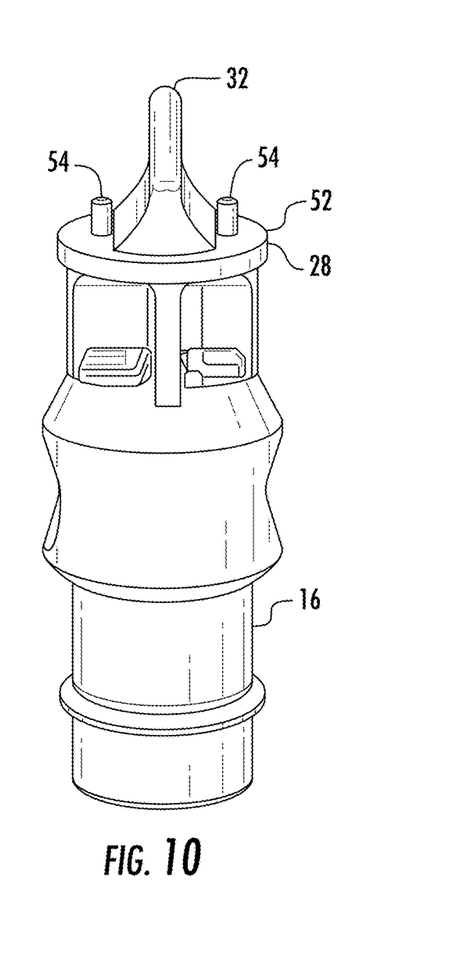
FIG. 10 is another perspective view of the drive coupling with force absorption system of FIG. 9.

In another embodiment of the force absorption system 14, as shown in FIGS. 8-10, the force absorption system 14 may be formed from a cylindrical proximal end 28 of the drive coupling 16 that includes an engagement protrusion 32 extending proximally from the proximal end 28 for engaging a drive shaft 22 of the drive system 10. The engagement protrusion 32 shown in FIG. 3 may be similar to the engagement protrusion 32 shown in FIGS. 3 and 4. The engagement protrusion 32 shown in FIG. 3 may extend proximally further than any other portion of the drive coupling 16. The engagement protrusion 32 shown in FIG. 3 may extend from a plate 52.

The force absorption system 14 shown in FIGS. 8-10 may include at least one force absorber 54 on the proximal end 28 of the drive coupling 16 on each side of the engagement protrusion 32 configured to contact a drive shaft 22. The force absorber 54 may be configured to enable linear movement of the drive coupling 16 along the longitudinal axis 18 of the drive coupling 16 while also providing resistance to such movement. As the drive coupling 16 moves further proximally against the force absorber 54, the amount of force imparted on the force absorber 54 against the drive coupling 16 increases. In at least one embodiment, the force absorber 54 may protrude proximally from the plate 52 forming a proximal end 28 to the drive coupling 16. In at least one embodiment, the force absorption system 14 may include two or more force absorbers 54. The force absorbers 54 may extend proximally from the proximal end 28 of the drive coupling 16 and may be positioned on opposing sides of the engagement protrusion 32. The force absorbers 54 may be formed from any appropriate material, such as, but not limited to plastic, metal, and pliable materials such as rubber. In at least one embodiment, a plastic force absorber 54 may be configured to be part of the drive couple 16. In at least one embodiment, the force absorber 54 may be a leaf spring.

Figure 11:
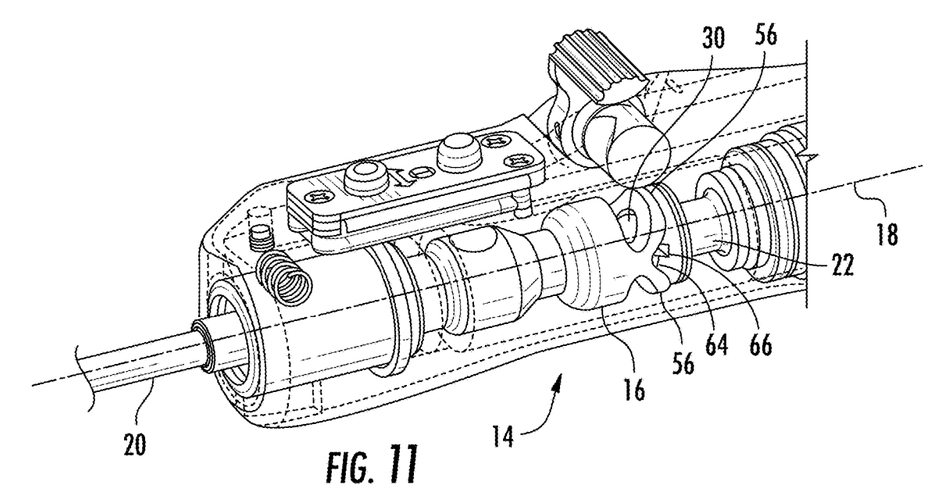
FIG. 11 is a cross-sectional view of a portion of the handheld rotary medical device of FIG. 1 with another embodiment of the force absorption system taken alone section line 2-2.
Figure 12:
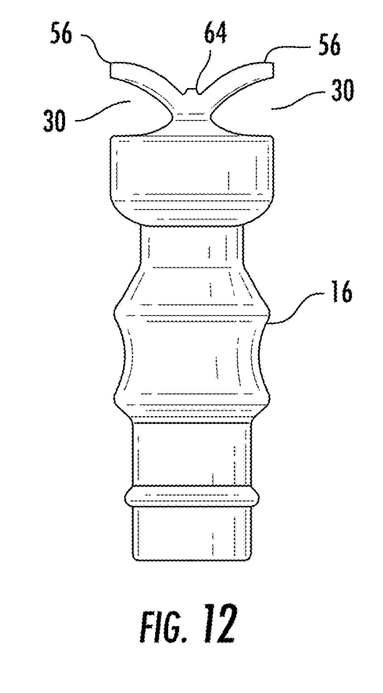
FIG. 12 is a side view of the drive coupling with force absorption system of FIG. 11.
Figure 13:
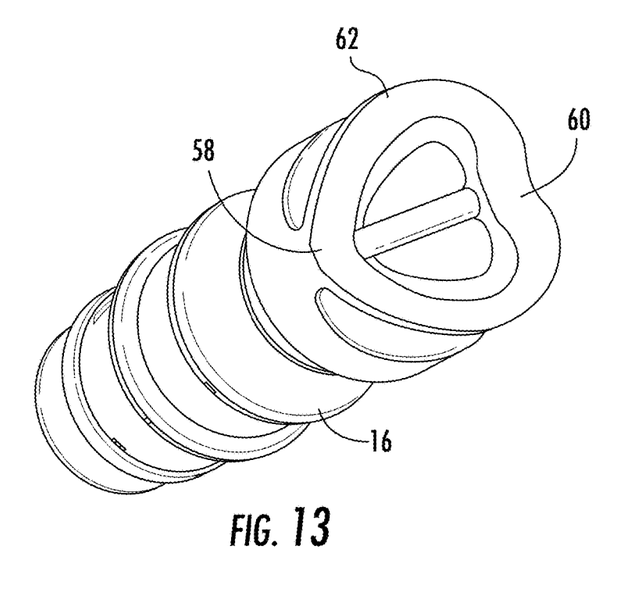
FIG. 13 is perspective view of the drive coupling with force absorption system of FIG. 11.

In another embodiment of the force absorption system 14, as shown in FIGS. 11-13, the force absorption system 14 may be formed from a hollow, cylindrical, proximal end 28 of the drive coupling 16, wherein material forming the hollow, cylindrical, proximal end 28 of the drive coupling 16 includes at least one relief slot 30 forming a wing 56. The wing 56 may be formed such that a width of the wing 56 in the proximal direction that is aligned with the longitudinal axis 18 of the drive coupling 16 is greater than a width of the adjacent relief slot measured in the same direction. The wing 56 may be curved moving circumferentially around the drive coupling 16. In particular, the wing 56 may extend from a first attachment point 58 circumferentially and proximally around a portion of the drive coupling 16 to a halfway point 62 between the first attachment point 58 and a second attachment point 60. From the halfway point 62 to the second attachment point 60, the wing 56 extends circumferentially and distally around a portion of the drive coupling 16 to the second attachment point 60. In at least one embodiment, the force absorption system 14 may include two or more wings 56. In an embodiment with two wings 56, the wings 56 may have identical lengths or differing lengths. The wings 56 may extend for less than three quarters of a circumference of the drive coupling. In at least one embodiment, the wings 56 may both have a length equal to or less than one half of a circumferential length of the drive coupling. In such a configuration, as shown in FIGS. 11-13, the wings may be nonlinear when viewed orthogonal to the longitudinal axis 18 of the drive coupling 16 and may form a groove 64 extending orthogonally to the longitudinal axis 18 of the drive coupling 16. When the drive coupling 16 is attached to a drive shaft 22, protrusions 66 may extend radially outward from the drive shaft 22 and reside within the groove 64 formed between the wings 56.

The drive coupling shown in FIGS. 11-13 may also include an engagement protrusion 32 positioned in the hollow, cylindrical, proximal end 28 for engaging a drive shaft 22 of the drive system 10. The engagement protrusion 32 shown in FIG. 4 may be similar to the engagement protrusion 32 shown in FIG. 1 and may be configured as set forth in the description above in connection with the engagement protrusion 32 in FIGS. 3 and 4.

Figure 14:
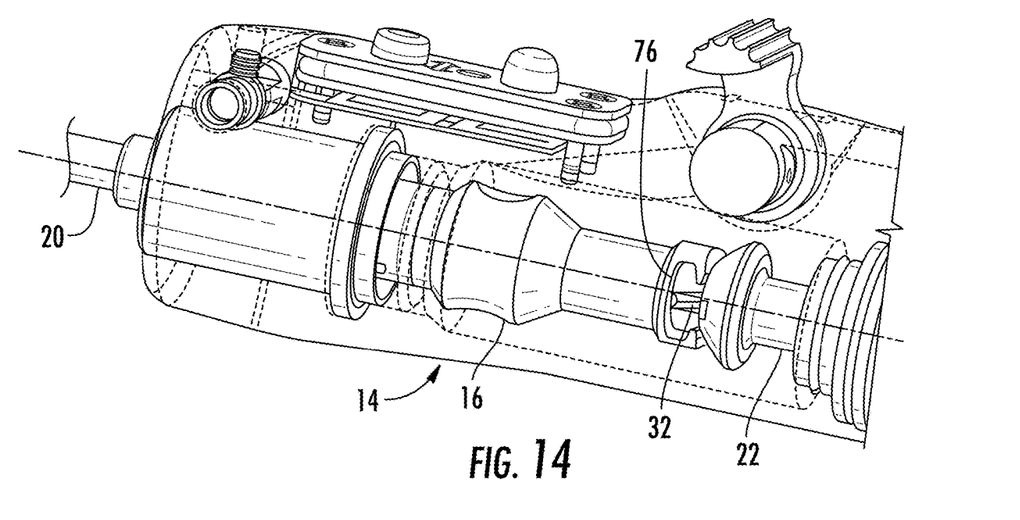
FIG. 14 is a cross-sectional view of a portion of the handheld rotary medical device of FIG. 1 with another embodiment of the force absorption system taken alone section line 2-2.
Figure 15:
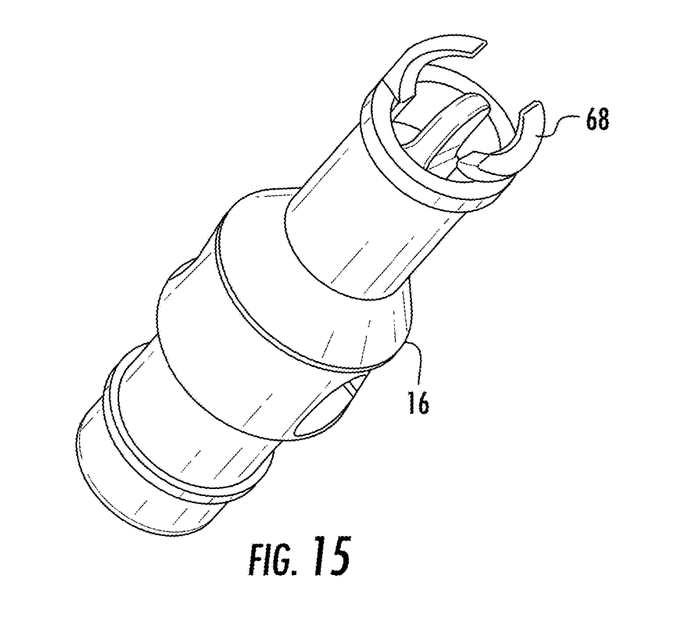
FIG. 15 is a perspective view of the drive coupling with force absorption system of FIG. 14.
Figure 16:
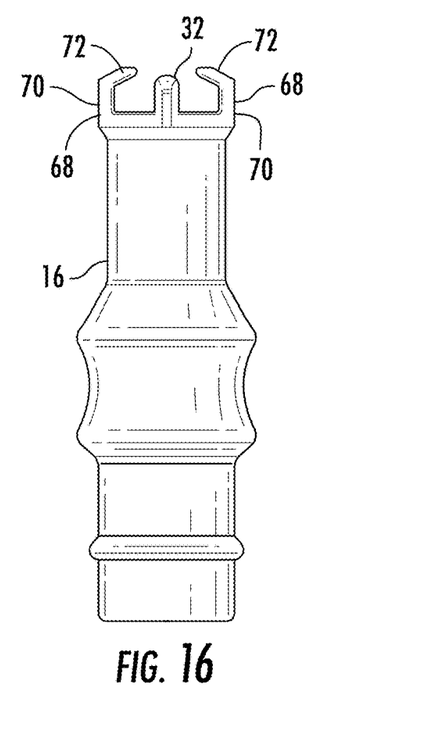
FIG. 16 is a side view of the proximal end of the drive coupling with force absorption system of FIG. 14.
Figure 17:
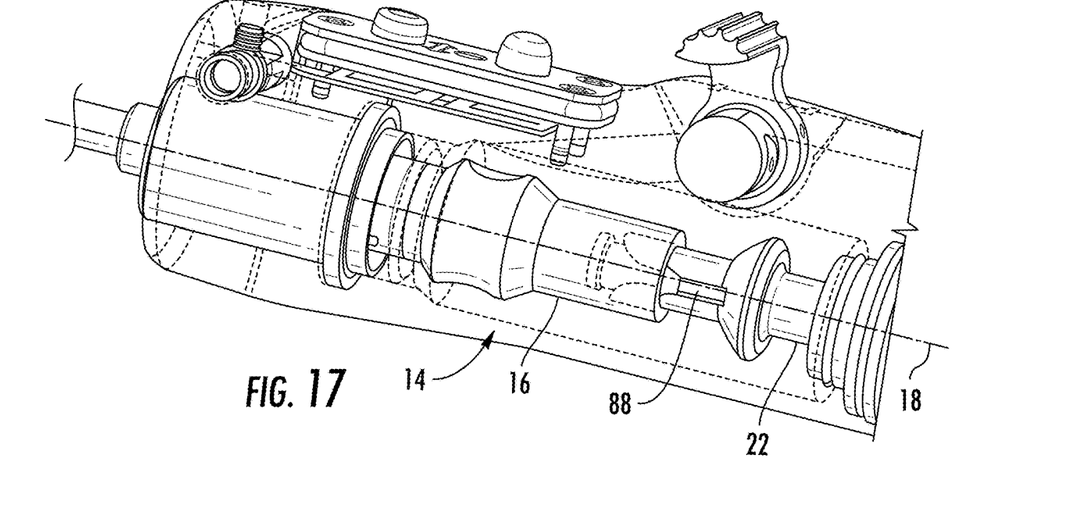
FIG. 17 is a cross-sectional view of a portion of the handheld rotary medical device of FIG. 1 with yet another embodiment of the force absorption system taken alone section line 2-2.
Figure 18:
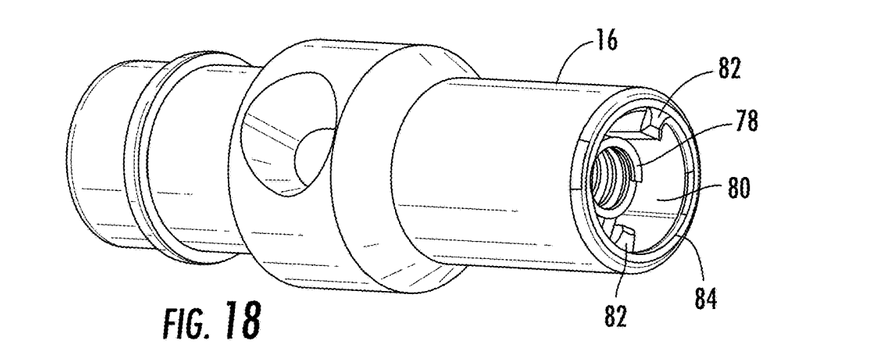
FIG. 18 is a perspective view of the drive coupling with force absorption system of FIG. 17.
Figure 19:
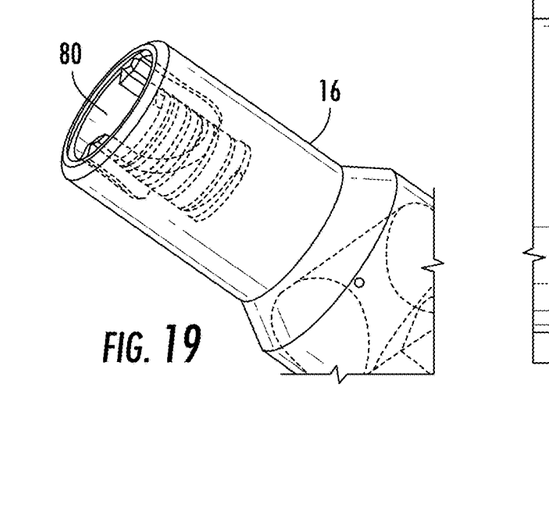
FIG. 19 is a partial perspective view of the proximal end of the drive coupling with force absorption system of FIG. 17.
Figure 20:
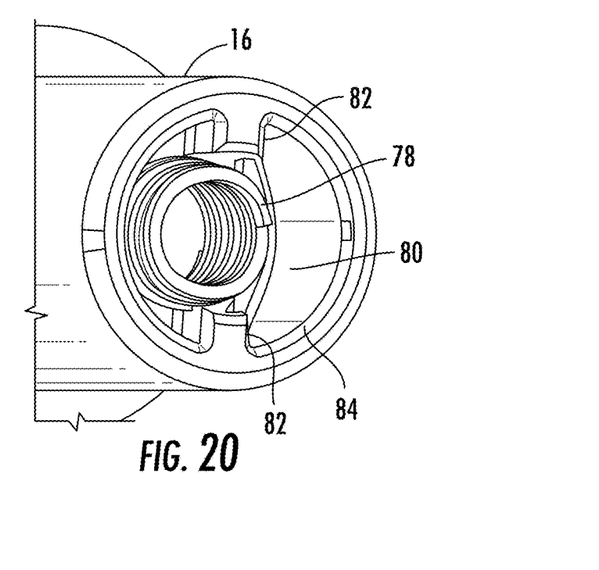
FIG. 20 is another partial perspective view of the proximal end of the drive coupling with force absorption system of FIG. 17.

In another embodiment of the force absorption system 14, as shown in FIGS. 14-16, the force absorption system 14 may be formed from a hollow, cylindrical, proximal end 28 of the drive coupling 16 and may include a plurality of pegs 68 extending proximally from a proximal end 28 of the drive coupling 16 and configured to contact a drive shaft 22 of the drive system 10. One or more of the pegs 68 may be formed from a base portion 70 that is aligned with the proximal end 28 of the drive coupling 16 and a tip portion 72 that is angled radially inward from the base portion 70. In at least one embodiment, the force absorption system 14 may include two pegs 68, each formed from the base portion 70 that is aligned with the longitudinal axis 18 of the drive coupling 16 and extending from the proximal end 28 of the drive coupling 16 and the tip portion 72 that is angled radially inward from the base portion 70. If the force absorption system 14 includes multiple pegs 68, the pegs 68 may be positioned equidistant from each other or in another manner. In an embodiment with four pegs 68, each of the pegs 68 may be positioned 180 degrees circumferentially from an adjacent peg 68 on the proximal end 28 of the drive coupling 16. In at least one embodiment, the base portion 70 of the peg 68 extends proximally from a proximal end 28 of the drive coupling 16 and extends from a periphery 76 of the proximal end 28. The thickness of the pegs 68 may be determined based upon the material used to form pegs 68 and anticipated linear forces applied to the drive coupling 16. The pegs 68 may be configured to flex radially outwardly to provide for limited linear movement of the drive coupling 16 while creating a linear force stored within the pegs 68 that when a force is removed from the drive coupling 16 forcing it in a proximal direction, the flexed pegs 68 move the drive coupling 16 linearly in a distal direction along the longitudinal axis 18 of the drive coupling 16.

The drive coupling shown in FIGS. 14-16 may also include an engagement protrusion 32 positioned in the hollow, cylindrical, proximal end 28 for engaging a drive shaft 22 of the drive system 10. The engagement protrusion 32 shown in FIG. 6 may be similar to the engagement protrusion 32 shown in FIG. 1 and may be configured as set forth in the description above in connection with the engagement protrusion 32 in FIGS. 3 and 4.

In another embodiment of the force absorption system 14, as shown in FIGS. 17-20, the force absorption system 14 may be formed from a hollow, cylindrical, proximal end 28 of the drive coupling 16, wherein a shock absorber 78 is positioned within a hollow chamber 80 of the proximal end 28 and exposed to contact a drive shaft 22 of the drive system 10. The shock absorber 78 may be positioned to contact the drive shaft 22 to provide for limited linear movement of the drive coupling 16 while creating a linear force stored within the shock absorber 78 that when a force is removed from the drive coupling 16 forcing it in a proximal direction, the shock absorber 78 moves the drive coupling 16 linearly in a distal direction along the longitudinal axis 18 of the drive coupling 16. The shock absorber 78 may be formed from any appropriate material and may be a coil spring. The force absorption system 14 may also include a plurality of tabs 82 extending radially inward from an inner surface 84 of the hollow chamber 80 to engage receivers 88 in the drive shaft 22 of the drive system. (FIG. 7) The tabs 82 may be any appropriate size and number to transmit rotary motion from the drive shaft 22 to the drive coupling 16. In at least one embodiment, the force absorption system 14 may include two tabs 82.

Figure 21:
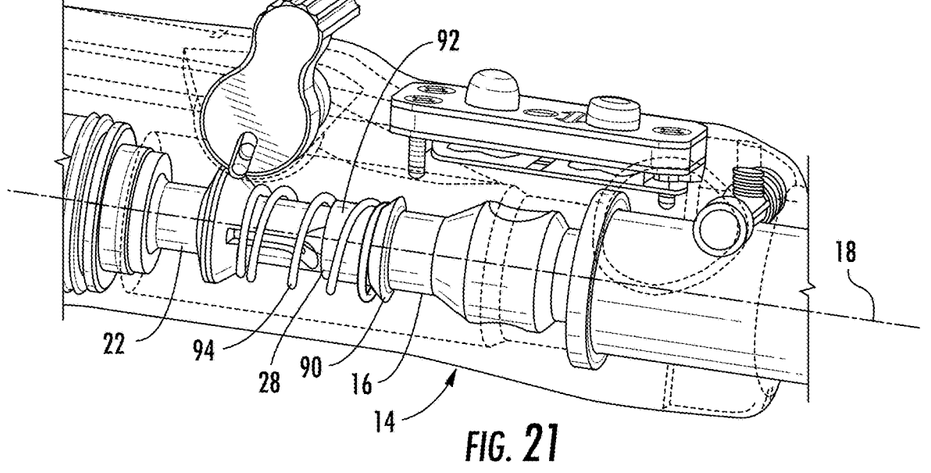
FIG. 21 is a cross-sectional view of a portion of the handheld rotary medical device of FIG. 1 with yet another embodiment of the force absorption system taken alone section line 3-3.
Figure 22:
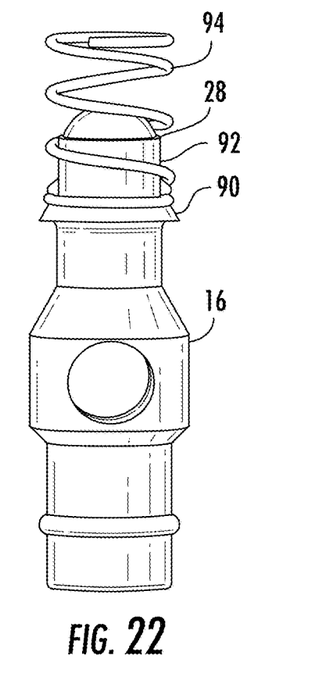
FIG. 22 is a side of the drive coupling with force absorption system of FIG. 21.
Figure 23:
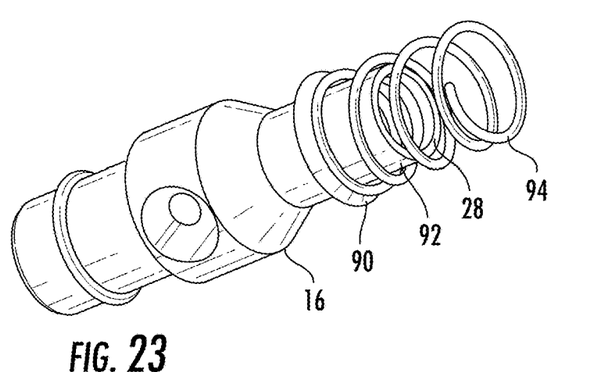
FIG. 23 is a perspective view of the proximal end of the drive coupling with force absorption system of FIG. 21.

In another embodiment of the force absorption system 14, as shown in FIGS. 21-23, the force absorption system 14 may be formed from a cylindrical, proximal end 28 of the drive coupling 16, a flange 90 extending radially outward from an outer surface 92 of the cylindrical, proximal end 28 of the drive coupling 16 and a shock absorber 94 coupled to the proximal end 28 of the drive coupling 16. The shock absorber 94 may extend around an outer surface of the drive coupling 16. The shock absorber 94 may bear against the flange 90 when the shock absorber 94 contacts the drive shaft 22. The shock absorber 94 may be formed from any appropriate material and may be a coil spring. In at least one embodiment, the coil spring 94 may at least partially encompass the drive coupling 16 at the proximal end 28.

The force absorption system 14 shown in FIG. 5 may be formed from a cylindrical proximal end 28 of the drive coupling 16 that includes an engagement protrusion 32 extending proximally from the proximal end 28 for engaging a drive shaft 22 of the drive system 10. The engagement protrusion 32 shown in FIG. 5 may be similar to the engagement protrusion 32 shown in FIG. 1. The engagement protrusion 32 shown in FIG. 5 may extend proximally further than any other portion of the drive coupling 16.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A drive system for a handheld rotary medical device, comprising:
    a drive coupling configured to be positioned between a drive motor and a rotary surgical implement;
    a force absorption system incorporated in the drive coupling whereby force absorption system absorbs linear forces aligned with a longitudinal axis of the drive coupling;
    wherein the force absorption system is formed from a hollow, cylindrical, proximal end of the drive coupling, wherein material forming the hollow, cylindrical, proximal end of the drive coupling includes a plurality of relief slots and an engagement protrusion positioned in the hollow, cylindrical, proximal end for engaging a drive shaft of the drive system;
    wherein longitudinal axes of the plurality of relief slots extend nonorthogonal and nonparallel relative to the longitudinal axis of the drive coupling.

2. The drive system of claim 1, wherein the relief slots form a helical configuration such that the relief slots are angled relative to the longitudinal axis of the drive coupling as the relief slots extend circumferentially around the drive coupling.

3. The drive system of claim 1, wherein the relief slots are aligned parallel to each other.

4. The drive system of claim 1, wherein at least one pair of the relief slots are misaligned relative to each other.

5. The drive system of claim 1, wherein the relief slots are offset from each other.

6. The drive system of claim 1, wherein at least one of the relief slots is elongated in shape.

7. The drive system of claim 1, wherein corners forming at least one of the relief slots are rounded.

8. The drive system of claim 1, wherein a circumferential length of at least one of the relief slots is between one eighth and three quarters of a circumferential length of the drive coupling.

9. The drive system of claim 1, wherein adjacent rows of relief slots are offset circumferentially between 20 degrees and 180 degrees.

10. A drive system for a handheld rotary medical device, comprising:
    a drive coupling configured to be positioned between a drive motor and a rotary surgical implement and having a proximal end separated from a distal end with at least one lateral side forming the drive coupling;
    a force absorption system incorporated in the drive coupling at the proximal end of the drive coupling whereby the force absorption system absorbs linear forces aligned with a longitudinal axis of the drive coupling;
    wherein the force absorption system is formed from a hollow, cylindrical, proximal end of the drive coupling, wherein material forming the hollow, cylindrical, proximal end of the drive coupling includes a plurality of relief slots forming wings extending radially outward and proximally from the proximal end of the drive coupling and an engagement protrusion positioned in the hollow, cylindrical, proximal end for engaging a drive shaft of the drive system, wherein the wings are positioned proximally of the relief slots, and the relief slots are positioned between the wings and the distal end of the drive coupling.

11. The drive system of claim 10, wherein a width of at least one of the wings in a proximal direction that is aligned with the longitudinal axis of the drive coupling is greater than a width of an adjacent relief slot measured in the same direction.

12. The drive system of claim 10, wherein at least one of the wings is curved moving circumferentially around the drive coupling.

13. The drive system of claim 10, wherein at least one of the wings extends from a first attachment point circumferentially and proximally around a portion of the drive coupling to a halfway point between the first attachment point and a second attachment point and from the halfway point to the second attachment point, the at least one wing extends circumferentially and distally around a portion of the drive coupling to the second attachment point.

14. The drive system of claim 10, wherein the wings have identical lengths.

15. The drive system of claim 10, wherein the wings have different lengths.

16. The drive system of claim 10, wherein at least one of the wings has a length equal to or less than one half of a circumferential length of the drive coupling.

17. The drive system of claim 10, wherein at least one of the wings is nonlinear when viewed orthogonal to the longitudinal axis of the drive coupling.

18. The drive system of claim 10, wherein the wings form a groove extending orthogonally to the longitudinal axis of the drive coupling.

19. The drive system of claim 18, wherein the groove is configured to receive protrusions extending radially outward from the drive shaft when the drive coupling is attached to a drive shaft.

* * * * *